US005843425A

United States Patent [19]
Sachs et al.

[11] Patent Number: 5,843,425
[45] Date of Patent: Dec. 1, 1998

[54] TRANSPLANTATION AND GRAFT-VERSUS-HOST-DISEASE

[75] Inventors: David H. Sachs, Newton; J. Scott Arn, North Andover, both of Mass.; Thomas Lorf, Hardegsen/Gladebeck, Germany

[73] Assignee: The General Hospital Corporation, Boston, Mass.

[21] Appl. No.: 461,693

[22] Filed: Jun. 5, 1995

Related U.S. Application Data

[63] Continuation-in-part of Ser. No. 266,427, Jun. 19, 1994, Pat. No. 5,614,182, Ser. No. 838,595, Feb. 19, 1992, abandoned, Ser. No. 451,210, May 26, 1995, abandoned, Ser. No. 220,371, Mar. 29, 1994, abandoned, Ser. No. 458,720, Jun. 1, 1995, Ser. No. 243,653, May 16, 1994, Pat. No. 5,658,564, Ser. No. 114,072, Aug. 30, 1993, Pat. No. 5,624,823, Ser. No. 150,739, Nov. 19, 1993, abandoned, and Ser. No. 212,228, Mar. 14, 1994, abandoned, said Ser. No. 451,210, is a continuation of Ser. No. 838,595.

[51] Int. Cl.$^6$ .............................. C12N 5/00; A61K 39/00
[52] U.S. Cl. ......................... 424/93.1; 435/331; 435/7.1; 424/93.21
[58] Field of Search ................................. 435/7.1, 240.2; 424/93.1, 93.21

[56] References Cited

PUBLICATIONS

Anasetti et al., "Treatment of Acute Graft–Versus–Host Disease with a Nonmitogenic Anti–CD3 Monoclonal Antibody", *Transplantation*, vol. 54, No. 5, pp. 844–851, (1992).
Beelan et al., "Treatment of Acute Graft–Versus–Host Disease After HLA–Partially Matched Marrow Transplanation with a Monoclonal Antibody (BMA031) Against the T Cell Receptor", *Onkologie*, vol. 11, pp. 56–58 (1988).
Blazer et al., "In vivo T–cell ligation facilitates alloengraftment and prevents lethal graft–versus–host disease (GVHD)", *Bone Marrow Transplant*, vol. 12 No. 3, pp. S38–40, (1993).
Cavazzana–Calvo et al., "Attenuation of Graft–Versus–Host Disease and Graft Rejection by Ex Vivo Immunotoxin Elimination of Alloreactive T cells in an H–2 Haplotype Disparate Mouse Combination", *Blood*, vol. 83, No. 1, pp. 288–298, (1994).
Charley et al., "Mechanism of Anti–asialo GM$_1$ Prevention of Graft–vs–Host Disease: Identification of Allo–antigen Activated T Cells", *The Journal of Investigative Dermatology*, vol. 91, No. 3, pp. 202–206, (1988).
Charlton et al., "CD4–positive/heart–stable antigen–positive thymocytes cause graft–*versus*–host disease across non–major histocompatibility complex imcompatibilities", *Eur. J. Immunol.*, vol. 24, No. 7, pp. 1706–1709, (1994).
Diamond et al., "Immunohistochemical Analysis of T Cell Phenotypes in Patients with Graft–Versus–Host Disease Following Allogeneic Bone Marrow Transplanation", *Transplanation*, vol. 59, No. 10, pp. 1436–1444, (1995).
Dietrich et al., "Analysis of T–Cell Receptor Variability in Transplanted Patients with Acute Graft–Versus–Host Disease", *Blood*, vol. 80, No. 9, pp. 2419–2424, (1992).
Elkins et al., "Study of a human minor alloantigen in relation to clinical graft–versus–host disease", *Bone Marrow Transplanation*. vol. 1, No. 4, pp. 397–403, (1987).
Fox et al., "Analysis of T Lymphocytes After Bone Marrow Transplanation Using Monoclonal Antibodies", *Blood*, vol. 60, No. 3, pp. 578–582, (1982).
Hess et al., "Cyclosporine–Induced Syngeneic Graft–vs–Host Disease: Prevention of Autoaggression by Treatment with Monoclonal Antibodies to T Lymphocyte Cell Surface Determinants and to MHC Class II Antigens", *Clinical Immunology and Immunopathology*, vol. 69, No. 3, pp. 341–430 (1993).
Holländer et al., "Loss of Normal Thymic Repertoire Selection and Persistence of Auto reactive T Cells in Graft vs Host Disease", *Journal of Immunology*, vol. 152, No. 4, pp.1609–1617, (1994).
Hosaka et al., "Attenuation of *lpr*–graft–*versus*–host disease (GVHD) in MRL*//pr* spleen cell–injected SCID mice by in vivo treatment with anti–Vβ8.1,2 monoclonal antibody", *Clin Exp Immunol.*, vol. 96, pp. 500–507, (1994).
Kernan et al., "Graft Failure After T–Cell–Depleted Human Leukocyte Antigen Identical Marrow Transplants for Leukemia: I. Analysis of Risk Factors and Results of Secondary Transplants", *Blood*, vol. 74, No. 6, pp. 2227–2236 (1989).
Maeda et al., "Amelioration of Acute Graft–Versus–Host Disease and Re–establishment of Tolerance by Short–Term Treatment with an Anti–TCR Antibody", *The Journal of Immunology*, vol. 153, No. 9, pp. 4311–4320, (1994).
Martin, "The role of donor lymphoid cells in allogeneic marrow engraftment", *Bone Marrow Transplantation*, vol. 6, pp. 282–289 (1990).
Martin et al., "Effects of treating marrow with a CD3–specific immunotoxin for prevention of acute graft–versus–host disease", *Bone Marrow Transplantation*, vol. 3, pp. 437–444 (1988), with Erratum, *Bone Marrow Transplanation*, vol. 4, p. 215, (1989) attached.
Mysliwietz et al., "Antilymphocytic Antibodies and marrow transplantation. XII. Suppression of Graft–Versus–Host Disease by T–Cell–Modulating and Depleting Antimouse CD3 Antibody is Most Effective When Preinjected in the Marrow Recipient", *Blood*, vol. 80, No. 10, pp. 2661–2667 (1992).

(List continued on next page.)

*Primary Examiner*—Jasemine C. Chambers
*Assistant Examiner*—Karen M. Hauda
*Attorney, Agent, or Firm*—Louis Meyers, Lahive & Cockfield

[57] ABSTRACT

A method of preparing swine donor tissue which includes hematopoietic stem cells and T cells for transplantation into a recipient mammal other than a swine. The method includes the swine donor tissue with an antibody which binds the epitope recognized by the mAb 2-6-15 monoclonal antibody. The binding facilitates depletion of T cells about as efficiently or more efficiently than does the mAb 2-6-15 monoclonal antibody and results in about the same or less depletion of stem cells as does the mAb 2-6-15 monoclonal antibody.

19 Claims, No Drawings

OTHER PUBLICATIONS

Nishimura et al., "Anti–idiotypic antibody to T–cell receptor in multiply transfused patients may play a role in resistance to graft–versus–host disease", *Transfusion*, vol. 32, No. 8., pp. 719–728 (1992).

Pennington et al., "Bone Marrow Transplantation in Miniature Swine", *Transplantation*, vol. 45, No. 1, pp. 21–26, (1988).

Racadot et al., "Prevention of Graft–Versus–Host Disease in HLA–Matched Bone Marrow Transplantation for Malignant Diseases: A Multicentric Study of 62 Patients Using 3–Pan–T Monoclonal Antibodies and Rabbit Complement", *Journal of Clinical Oncology*, vol. 5, No. 3, pp. 426–435, (1987).

Roy et al., "The Immunopathology of Upper Gastrointestinal Acute Graft–Versus–Host Disease" *Transplanation*, vol. 55, No. 3, pp. 572–578, (1993).

Schattenfroh et al., "Phenotypic Analysis of Donor Cells Infiltrating the Small Intestinal Epithelium and Spleen During Graft–Versus–Host Disease", *Transplanation*, vol. 59, No. 2, pp. 268–273 (1995).

Schneider et al., "Acute Graft–versus–Host Reaction in SCID Mice Leads to an Abnormal Expansion of CD8+ V$\beta$14+ and a Broad Inactivation of Donor T Cells Followed by a Host–Restricted Tolerance and a Normalization of the TCR V$\beta$ Repertoire in hte Chronic Phase", *Scand. J. Immunol.*, vol 41, pp. 373–383, (1995).

van Els et al., Graft–versus–host disease associated T helper responses specific for minor histocompatibility antigens are mainly restricted by HLA–DR molecules, *Bone Marrow Transplantation*, vol. 5, pp. 365–372, (1990).

TRANSPLANTATION AND GRAFT-VERSUS-HOST-DISEASE

RELATED APPLICATIONS

This application is a continuation-in-part of: U.S. Ser. No. 08/266,427, filed Jun. 27, 1994, 1993, patented U.S Pat. No. 5,614,182; U.S. Ser. No. 07/838,595, filed Feb. 19, 1992, now abandoned; U.S. Ser. No. 07/451,210, filed May 26, 1995, now abandoned, which is a File Wrapper Continuation of U.S. Ser. No. 07/838,595, filed Feb. 19, 1992 now abandoned; U.S. Ser. No. 08/220,371, filed Mar. 29, 1994, now abandoned; PCT/US94/05527, filed May 16, 1994; U.S. Ser. No. 08/458,720, filed Jun. 1, 1995, which is a continuation-in-part of PCT/US94/05527; U.S. Ser. No. 08/243,653, filed May 16, 1994, now patented, U.S. Pat. No. 5,658,569; U.S. Ser. No. 08/114,072, filed Aug. 30, 1993, patented, U.S. Pat. No. 5,624,823; U.S. Ser. No. 08/150,739, filed Nov. 10, 1993, now abandoned; U.S. Ser. No. 08/212,228, filed Mar. 14, 1994, now abandoned; and PCT/US94/01616 filed Feb. 14, 1994. All of the above-recited patent applications are hereby incorporated by reference.

BACKGROUND OF THE INVENTION

The invention relates to tissue and organ transplantation.

SUMMARY OF THE INVENTION

The inventors have discovered that antibodies which bind swine T cell antigens, e.g., the T cell surface antigen 2-6-15, are particularly effective for depleting T cells, and that these anti-T cell antibodies can be used to, e.g., deplete swine T cells in recipients of transplanted swine tissue, e.g., transplanted stem cells, thereby inhibiting graft-versus-host-disease (GVHD) in the recipients.

Accordingly, the invention features a method of preparing donor tissue, e.g., hematopoietic stem cells, e.g., bone marrow cells, cord blood cells, fetal liver or spleen cells, for transplantation into a recipient mammal, e.g., a primate, e.g., a human. The method includes: contacting the donor tissue, e.g., donor hematopoietic stem cells, with an antibody, e.g., a monoclonal antibody, which binds a T cell antigen, e.g. the T cell antigen 2-6-15.

In preferred embodiments: the tissue is swine tissue, e.g., swine stem cells, and the recipient is a mammal other than a swine, e.g., a primate, e.g., a non-human primate or a human; the hematopoietic stem cells are obtained from a miniature swine.

In a preferred embodiment, the tissue is swine bone marrow cells and the antibody is an antibody fragment, e.g., a Fab fragment, a monoclonal antibody, a polyclonal antibody, a humanized antibody, a chimeric antibody, a recombinantly produced antibody, or a derivatized antibody.

In a preferred embodiment, the antibody binds the swine t cell antigen 2-6-15.

The percentage of T cells in the preparation to be deleted varies, but generally is at least about 80%, more preferably at least about 90%, yet more preferably at least about 95%, and most preferably at least about 98% of the T cells in the preparation. It may be desirable to totally deplete the T cells in a stem cell preparation and then to reconstitute the preparation by adding a defined number of donor T cells, or by adding defined classes of T cells to the preparation.

Treatment will generally result in depletion of less than about 30%, preferably about 20%, more preferably about 10%, and most preferably about 5% of the hematopoietic stem cells of the preparation.

In another aspect, the invention features, a preparation of a swine tissue, e.g., swine hematopoietic stem cells, and an antibody, preferably other than a swine antibody, which binds a swine T cell antigen.

In preferred embodiments, the swine hematopoietic stem cells are obtained from a miniature swine; the swine hematopoietic stem cells are swine bone marrow cells and the antibody binds the swine 2-6-15 antigen; the antibody is the antibody of ATCC deposit HB1.1914.

In another aspect, the invention features a preparation of T cell-depleted swine tissue, e.g., swine hematopoietic stem cells, e.g., swine bone marrow cells.

In preferred embodiments, the T cells are depleted by contact with an antibody, e.g., an antibody which binds a T cell antigen, e.g., the swine 2-6-15 antigen, e.g., the antibody of ATCC deposit HB11914.

The percentage of T cells in the preparation to be deleted varies, but generally is at least about 80%, more preferably at least about 90%, yet more preferably at least about 95%, and most preferably at least about 98% of the F cells in the preparation. It may be desirable to totally deplete the T cells in a stem cell preparation and then to reconstitute the preparation by adding a defined number of donor T cells, or by adding defined classes of T cells to the preparation.

Treatment will generally result in depletion of less than about 30%, preferably about 20%, more preferably about 10%, and most preferably about 5% of the hematopoietic stem cells of the preparation.

Methods of inhibiting GVHD described herein can be combined with various methods for inducing tolerance, e.g., methods described in U.S. Ser. No. 07/838,595.

Accordingly, in another aspect, the invention features a method of inhibiting GVHD in a mammal, e.g., a primate, e.g., a human, which is the recipient of a graft, e.g., an allograft or xenograft, e.g., a swine graft. The method includes: preferably prior to or simultaneous with introduction of the graft, introducing into the recipient mammal, hematopoietic stem cells, e.g., bone marrow cells, cord blood cells, fetal liver or spleen cells (preferably the hematopoietic stem cells home to a site in the recipient mammal); preferably, implanting the graft into the recipient mammal; and, preferably, administering to the recipient an antibody, preferably a monoclonal antibody, which binds a T cell antigen.

In preferred embodiments, the recipient is a mammal other than a swine, e.g., a primate, e.g., a non-human primate or a human primate, the graft is from a swine, e.g., a miniature swine, and the antibody binds the swine 2-6-15 antigen.

In a preferred embodiment, the graft is obtained from a different organ than the swine hematopoietic stem cells, e.g., a liver or a kidney.

In a preferred embodiment, the hematopoietic stem cells are introduced into the recipient mammal by injection, e.g., intravenous injection.

In preferred embodiments, the antibody is an antibody fragment, e.g., a Fab fragment, a monoclonal antibody, a polyclonal antibody, a humanized antibody, a chimeric antibody, a recombinantly produced antibody, or a derivatized antibody.

In preferred embodiments, the antibody is administered to the recipient mammal 0 to 5 or 10 days before introduction of the graft.

In preferred embodiments, the antibody is administered to the recipient mammal 0 to 5 or 10 days before introduction of the graft.

In preferred embodiments, the antibody is administered to the recipient mammal when symptoms of GVHD are observed in the recipient.

In preferred embodiments, the antibody is administered to the recipient mammal until alleviation of the symptoms of GVHD is observed in the recipient.

In preferred embodiments, administration of the antibody is repeated one, two, three, four, or more times.

The antibody is administered to the recipient mammal through a route of administration which allows the antibody to perform its intended function, e.g., to deplete donor T cells. Preferred routes of antibody administration include injection, e.g., intravenous injection, subcutaneous injection, or intraperitoneal injection. Depending on the route of administration, the antibody can be coated with or in a material to protect it from the natural conditions which may detrimentally affect its ability to perform its intended function. The administration of the antibody is done at dosages and for periods of time effective to induce tolerance in the recipient to the swine graft. Dosage regimens may be adjusted for purposes of improving the therapeutic response of the antibody. For example, several divided doses can be administered daily or the dose may be proportionally reduced as indicated by the exigencies of the therapeutic situation.

In other preferred embodiments, the method includes: (preferably prior to or at the time of introducing the hematopoietic stem cells into the recipient) depleting, inactivating or inhibiting recipient natural killer (NK) cells, e.g., by introducing into the recipient an antibody capable of binding to NK cells of the recipient, to prevent NK mediated rejection of the swine graft. One source of anti-NK antibody is anti-human thymocyte polyclonal anti-serum. Preferably, a second anti-mature T cell antibody can be administered as well, which uses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

In other preferred embodiments, the method includes: (preferably prior to or at the time of introducing the hematopoietic stem cells into the recipient) depleting, inactivating or inhibiting host T cell function, e.g., by introducing into the recipient an antibody capable of binding to T cells of the recipient; (preferably prior to or at the time of introducing the thymic tissue into the recipient) depleting, inactivating or inhibiting host $CD4^+$cell function, e.g., by introducing into the recipient an antibody capable of binding to CD4, or $CD4^+$cells of the recipient.

Other preferred embodiments include: the step of creating hematopoietic space, e.g., by one or more of, irradiating the recipient with low dose, e.g., between about 100 and 400 rads, whole body irradiation, administering a myelosuppressive drug to the recipient, or administering anti-class I antibodies to the recipient, to deplete or partially deplete the bone marrow of the recipient; the method includes the a step which creates hematopoietic space and the step is performed prior to introducing the swine hematopoietic stem cells into the recipient.

Other preferred embodiments include inactivating thymic T cells by one or more of: (preferably prior to hematopoietic stem cell transplantation) irradiating the recipient mammal with, e.g., about 700 rads of thymic irradiation; administering one, or preferably two or more, doses of an anti-T cell antibody; or administering to the recipient a short course of an immunosuppressant as described in U.S. Ser. No. 08/220,371, filed Mar. 29, 1994.

Other preferred embodiments include: the step of depleting or otherwise inactivating natural antibodies in the blood of the recipient mammal, e.g., by hemoperfusing an organ, e.g., a liver or a kidney, obtained from the donor species, e.g., from a swine, or administering a drug, e.g., deoxyspergualin (DSG) which inactivates or depletes natural antibodies; the method includes a step which depletes or otherwise inactivates natural antibodies in the blood of the recipient and the step is performed prior to hematopoietic stem cell transplantation.

Other preferred embodiments include: the step of introducing into the recipient mammal, donor, e.g, swine stromal tissue, preferably hematopoietic stromal tissue, e.g., fetal liver or thymus. In preferred embodiments: the stromal tissue is introduced simultaneously with, or prior to, the hematopoietic stem cells; the bone marrow cells are introduced simultaneously with, or prior to, any anti-NK or T cell antibody.

Other preferred embodiments include those in which the donor is a swine and: the same swine is the donor of both the graft and the hematopoietic cells; and the antibody is an anti-human thymocyte polyclonal anti-serum, obtained, e.g., from a horse or pig.

The methods for inhibiting GVHD in a recipient mammal described herein can be combined with yet other methods for inducing tolerance, e.g., with: methods which use the implantation of a xenogeneic thymic graft to induce tolerance, e.g., the methods described in U.S. Ser. No. 08/243,653, filed May 16, 1994; methods of increasing the level of the activity of a tolerance promoting or GVHD inhibiting cytokine or decreasing the level of activity of a tolerance inhibiting or GVHD promoting cytokine, e.g., the methods described in U.S. Ser. No. 08/114,072, filed Aug. 30, 1993; methods of using cord blood cells to induce tolerance, e.g., the methods described in U.S. Ser. No. 08/150,739 filed Nov. 10, 1993; and the methods for inducing tolerance disclosed in Sykes and Sachs, PCT/US94/01616, filed Feb. 14, 1994. In other preferred embodiments the method further includes administering to the recipient a short course of help reducing treatment, e.g., a short course of high dose cyclosporine, as is described in U.S. Ser. No. 8/220,371, filed Mar. 24, 1994.

In another aspect, the invention features a method of inhibiting GVHD in a mammal, e.g., a primate, e.g., a human, which is the recipient of a donor graft, e.g., an allograft or a xenograft. The method includes contacting donor hematopoietic stem cells, e.g., bone marrow cells, cord blood cells, fetal liver or spleen cells, with an antibody which binds a T cell antigen, e.g, the 2-6-15 antigen; introducing the antibody-treated donor stem cells into the recipient mammal; and (preferably) implanting the graft into the recipient mammal.

In preferred embodiments, the stem cells are swine stem cells and the recipient is a mammal other than a swine, e.g., a primate, e.g., a non-human primate or a human.

Depletion of donor T cells present in a stem cell preparation can decrease the propensity of the preparation to induce GVHD. However, since excessive depletion of T cells can result in a stem cell preparation with less than optimal tolerance-inducing abilities, the degree of T cell depletion should be controlled so as to obtain a balance between the tolerance-inducing capacity and the propensity to induce GVHD. Control can be exerted, e.g., by the concentration of the antibodies used. The percentage of T cells to be deleted varies, but generally is at least about 80%, more preferably at least about 90%, yet more preferably at least about 95%, and most preferably at least about 90% of the T cells in the preparation. It may be desirable to totally deplete the T cells in a stem cell preparation and then to reconstitute the preparation by adding a defined number of donor T cells, or by adding defined classes of T cells to the preparation.

Treatment will generally result in depletion of less than about 30%, preferably about 20%, more preferably about 10%, and most preferably about 5% of the hematopoietic stem cells of the preparation.

In a preferred embodiment, the graft is obtained from a different organ than the hematopoietic stem cells, e.g., liver or kidney.

In preferred embodiments, the hematopoietic stem cells are introduced into the recipient mammal by injection, e.g., intravenous injection.

In preferred embodiments, the antibody is an antibody fragment, e.g., a monoclonal antibody, a polyclonal antibody, a humanized antibody, a chimeric antibody, a recombinantly produced antibody, or a derivatized antibody.

In other preferred embodiments, the method includes: (preferably prior to or at the time of introducing the bone marrow cells tissue into the recipient) depleting, inactivating or inhibiting recipient natural killer (NK) cells, e.g., by introducing into the recipient an antibody capable of binding to NK cells of the recipient, to prevent NK mediated rejection of the host donor tissue; (preferably prior to or at the time of introducing the bone marrow cells into the recipient) depleting, inactivating or inhibiting host T cell function, e.g., by introducing into the recipient an antibody capable of binding to T cells of the recipient; (preferably prior to or at the time of introducing the thymic tissue into the recipient) depleting, inactivating or inhibiting host CD4+ cell function, e.g., by introducing into the recipient an antibody capable of binding to CD4, or CD4+ cells of the recipient.

Other preferred embodiments include: the step of creating hematopoietic space, e.g., by one or more of, irradiating the recipient with low dose, e.g., between about 100 and 400 rads, whole body irradiation, administering a myleosuppressive drug to the recipient, or administering anti-class I antibodies to the recipient, to deplete or partially deplete the bone marrow of the recipient; the method includes the a step which creates hematopoietic space and the step is performed prior to introducing the donor bone marrow cells into the recipient.

Other preferred embodiments include inactivating thymic T cells by one or more of: (preferably prior to hematopoietic stem cell transplantation) irradiating the recipient mammal with, e.g., about 700 rads of thymic irradiation; administering one, or preferably two or more, doses of an anti-T cell antibody; or administering to the recipient a short course of an immunosuppressant as described in U.S. Ser. No. 08/220, 371, filed Mar. 29, 1994.

Other preferred embodiments include: the step of depleting or otherwise inactivating natural antibodies in the blood of the recipient mammal, e.g., by hemoperfusing an organ, e.g., a liver or a kidney, obtained from a donor species, e.g., a pig, or administering a drug, e.g., deoxyspergualin (DSG) which inactivates or depletes natural antibodies; the method includes a step which depletes or otherwise inactivates natural antibodies in the blood of the recipient and the step is performed prior to hematopoietic stem cell transplantation.

In preferred embodiments, the method includes the step of introducing into the recipient a graft obtained from the donor which is obtained from a different organ than the liematopoietic stem cells, e.g., a liver or a kidney.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the bone marrow cells are introduced simultaneously with, or prior to, any anti-NK or T cell antibody.

Other preferred embodiments include those in which: the same mammal of the second species is the donor of one or both the graft and the hematopoietic cells; and the antibody is an anti-human thymocyte polyclonal anti-serum, obtained, e.g., from a horse or pig.

Methods of inhibiting GVHD can be combined with yet other methods for inducing tolerance, e.g., with: methods which use the implantation of a xenogeneic thymic graft to induce tolerance, e.g., the methods described in U.S. Ser. No. 08/243,653, filed May 16, 1994; methods of increasing the level of the activity of a tolerance promoting or GVHD inhibiting cytokine or decreasing the level of activity of a tolerance inhibiting or GVHD promoting cytokine, e.g., the methods described in U.S. Ser. No. 08/114,072, filed Aug. 30, 1993; methods of using cord blood cells to induce tolerance, e.g., the methods described in U.S. Ser. No. 08/150,739 filed Nov. 10, 1993; and the methods for inducing tolerance disclosed in Sykes and Sachs, PCT/US94/ 01616, filed Feb. 14, 1994. In other preferred embodiments the method further includes administering to the recipient a short course of help reducing treatment, e.g., a short course of high dose cyclosporine, as is described in U.S. Ser. No. 8/220,371, filed Mar. 24, 1994.

In another aspect, the invention features a method of inhibiting GVHD in a mammal, e.g., a primate, e.g., a human, which is the recipient of a donor graft, e.g., an allograft or a xenograft, e.g., a miniature swine graft. The method includes contacting hematopoietic stem cells, e.g., bone marrow cells, cord blood cells, fetal liver or spleen cells, with an antibody which binds a T cell antigen, e.g., the 2-6-15 antigen; implanting the antibody-treated stem cells into the recipient mammal; introducing the graft into the recipient mammal; and administering to the recipient an antibody, preferably a monoclonal antibody, which binds, a T cell antigen, e.g., the 2-6-15 antigen of the donor species.

In preferred embodiments, the stem cells are swine stem cells, the graft is a swine graft, and the recipient is a mammal other than a swine, e.g., a primate, e.g., a non-human primate or a human.

Depletion of donor T cells present in a stem cell preparation can decrease the propensity of the preparation to induce GVHD. However, since excessive depletion of T cells can result in a stem cell preparation with less than optimal tolerance-inducing abilities, the degree of T cell depletion should be controlled so as to obtain a balance between the tolerance-inducing capacity and the propensity to induce GVHD. Control can be exerted, e.g., by the concentration of the antibodies used.

The percentage of T cells to be deleted varies, but generally is at least about 80%, more preferably at least about 90%, yet more preferably at least about 95%, and most preferably at least about 98% of the T cells in the preparation. It may be desirable to totally deplete the T cells in a stem cell preparation and then to reconstitute the preparation by adding a defined number of donor T cells, or by adding defined classes of T cells to the preparation.

In preferred embodiments, the antibody is administered to the recipient mammal 0 to 5 or 10 days before introduction of the graft.

In preferred embodiments, the antibody is administered to the recipient mammal 0 to 5 or 10 days before introduction of the graft.

In preferred embodiments, the antibody is administered to the recipient mammal after symptoms of GVHD are observed in the recipient.

In preferred embodiments, the antibody is administered to the recipient mammal until alleviation of the symptoms of GVHD is observed in the recipient.

In preferred embodiments, administration of the antibody is repeated one, two, three, four, or more times.

In preferred embodiments, the antibody is an antibody fragment, e.g., a monoclonal antibody, a polyclonal antibody, a humanized antibody, a chimeric antibody, a recombinantly produced antibody, or a derivatized antibody.

The antibody can be administered to the recipient mammal through a route of administration which allows the antibody to perform its intended function, e.g., deplete T cells from swine hematopoietic stem cells. Preferably, the antibody is administered at a level such that the ability of the swine hematopoietic stem cells to induce tolerance is maximized. (e.g., GVHD is minimized). Preferred routes of antibody administration include injection, e.g., intravenous injection, subcutaneous injection, or intraperitoneal injections. Depending on the route of administration, the antibody can be coated with or in a material to protect it from the natural conditions which may detrimentally affect its ability to perform its intended function. The administration of the antibody is done at dosages and for periods of time effective to significantly reduce or eliminate the symptoms associated with CF. Dosage regimes may be adjusted for purposes of improving the therapeutic response of the antibody. For example, several divided doses can be administered daily or the dose may be proportionally reduced as indicated by the exigencies of the therapeutic situation In a preferred embodiment, the graft is obtained from a different organ than the hematopoietic stem cells, e.g., liver or kidney.

In preferred embodiments, the hematopoietic stem cells are introduced into the recipient mammal by injection, e.g., intravenous injection.

In preferred embodiments, the antibody is an antibody fragment, e.g., , a monoclonal antibody, a polyclonal antibody, a humanized antibody, a chimeric antibody, a recombinantiy produced antibody, or a derivatized antibody.

In other preferred embodiments, the method includes: (preferably prior to or at the time of introducing the bone marrow cells tissue into the recipient) depleting, inactivating or inhibiting recipient natural killer (NK) cells, e.g., by introducing into the recipient an antibody capable of binding to NK cells of the recipient, to prevent NK mediated rejection of the host donor tissue; (preferably prior to or at the time of introducing the bone marrow cells into the recipient) depleting, inactivating or inhibiting host T cell function, e.g., by introducing into the recipient an antibody capable of binding to T cells of the recipient; (preferably prior to or at the time of introducing the thymic tissue into the recipient) depleting, inactivating or inhibiting host $CD4^+$ cell function, e.g., by introducing into the recipient an antibody capable of binding to CD4, or $CD4^+$ cells of the recipient.

Other preferred embodiments include: the step of creating hematopoietic space, e.g., by one or more of, irradiating the recipient with low dose, e.g., between about 100 and 400 rads, whole body irradiation, administering a myleosuppressive drug to the recipient, or administering anti-class I antibodies to the recipient, to deplete or partially deplete the bone marrow of the recipient; the method includes the a step which creates hematopoietic space and the step is performned prior to introducing the donor bone marrow cells into the recipient.

Other preferred embodiments include inactivating thymic T cells by one or more of: (preferably prior to hematopoietic stem cell transplantation) irradiating the recipient mammal with, e.g., about 700 rads of thymic irradiation; administering one, or preferably two or more, doses of an anti-T cell antibody; or administering to the recipient a short course of an immunosuppressant as described in U.S. Ser. No. 08/220, 371, filed Mar. 29, 1994.

Other preferred embodiments include: the step of depleting or otherwise inactivating natural antibodies in the blood of the recipient mammal, e.g., by hemoperfusing an organ, e.g., a liver or a kidney, obtained from, the donor species, e.g., a pig, or administering a drug, e.g., deoxyspergualin (DSG) which inactivates or depletes natural antibodies; the method includes a step which depletes or otherwise inactivates natural antibodies in the blood of the recipient and the step is performed prior to hematopoietic stem cell transplantation.

In preferred embodiments, the method includes the step of introducing into the recipient a graft obtained from the donor which is obtained from a different organ than the hematopoietic stem cells, e.g., a liver or a kidney.

One source of anti-NK antibody is anti-human thymocyte polyclonal anti-serum. Preferably, a second anti-mature T cell antibody can be administered as well, which uses T cells as well as NK cells. Lysing T cells is advantageous for both bone marrow and xenograft survival. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the bone marrow cells are introduced simultaneously with, or prior to, any anti-NK or T cell antibody.

Other preferred embodiments include those in which: the same mammal of the second species is the donor of one or both the graft and the hematopoictic cells; and the antibody is an anti-human thymocyte polyclonal anti-serum, obtained, e.g., from a horse or pig.

Methods of inhibiting GVHD can be combined with yet other methods for inducing tolerance, e.g., with: methods which use the implantation of a xenogeneic thymic graft to induce tolerance, e.g., the methods described in U.S. Ser. No. 08/243,653, filed May 16, 1994; methods of increasing the level of the activity of a tolerance promoting or GVHD inhibiting cytokine or decreasing the level of activity of a tolerance inhibiting or GVHD promoting cytokine, e.g., the methods described in U.S. Ser. No. 08/114,072, filed Aug. 30, 1993; methods of using cord blood cells to induce tolerance, e.g., the methods described in U.S. Ser. No. 08/150,739 filed Nov. 10, 1993; and the methods for inducing tolerance disclosed in Sykes and Sachs, PCT/US94/01616, filed Feb. 14, 1994. In other preferred embodiments the method further includes administering to the recipient a short course of help reducing treatment, e.g., a short course of high dose cyclosporine, as is described in U.S. Ser. No. 8/220,371, filed Mar. 24, 1994.

The invention also includes a purified preparation of an antibody which is specific for the 2-6-15 antigen, e.g., mAb 2-6-15 or an antibody with similar properties, as well as hybridomas which produce such antibodies.

"Lymph node or thymic T cell", as used herein, refers to T cells which are resistant to inactivation by traditional methods of T cell inactivation, e.g., inactivation by a single intravenous administration of anti-T cell antibodies, e.g., anti-bodies, e.g., ATG preparation.

"Tolerance", as used herein, refers to the inhibition of a graft recipient's immune response which would otherwise occur, e.g., in response to the introduction of a nonself MHC antigen into the recipient. Tolerance can involve humoral, cellular, or both humoral and cellular responses.

"Hematopoietic stem cell", as used herein, refers to a cell, e.g., a bone marrow cell which is capable of developing into a mature myeloid and/or lymphoid cell. Stem cells derived from the cord blood of the recipient or the donor can be used in methods of the invention. See U.S. Pat. No. 5,192,553, hereby incorporated by reference, and U.S. Pat. No. 5,004,681, hereby incorporated by reference.

"Miniature swine", as used herein, refers to wholly or partially inbred animal.

"Graft", as used herein, refers to a body part, organ, tissue, or cells. Grafts may consist of organs such as liver, kidney, heart or lung; body parts such as bone or skeletal matrix; tissue such as skin, intestines, endocrine glands; or progenitor stem cells of various types.

"A discordant species combination", as used herein, refers to two species in which hyperacute rejection occurs when a graft is grafted from one to the other. Generally, discordant species are from different orders, while non-discordant species are from the same order. For example, rats and mice are non-discordant species, i.e. their MHC antigens are substantially similar, and they are members of the same order, rodentia.

"Stromal tissue", as used herein, refers to the supporting tissue or matrix of an organ, as distinguished from its functional elements or parenchyma.

Other features and advantages of the invention will be apparent from the following detailed description, and from the claims.

DETAILED DESCRIPTION

I. Preparation of Antibodies

A. Immunization

An antibody of the invention is typically prepared by immunizing a suitable subject with an appropriate immunogenic preparation and isolating an antibody having the characteristics described herein. An appropriate immunogenic preparation can contain, for example, whole swine T cells, the 2-6-15 antigen, or the 2-6-15 antigen combined with a liposome, a membrane fragment, or other bilayer structure.

The 2-6-15 antigen can be prepared by methods known to those skilled in the art using mAb 2-6-15.

The unit dose of immunogenic preparation and the immunization regimen will depend upon the species of mammal immunized, its immune status, the body weight of the mammal and the 2-6-15 antigen content of the immunogenic preparation administered. The immunized subject is generally a mouse. An example of the preparation of the 2-6-15 antibody is given below.

Immunization of a subject with a whole T cell, the 2-6-15 antigen, or the 2-6-15 antigen combined with a liposome, a membrane fragment, or other bilayer structure preparation as described above generally induces a variety of anti-swine T cell antibodies. The anti-2-6-15 antibody titer in the immunized subject can be monitored over time by standard techniques, such as with an enzyme linked immunosorbent assay (ELISA) using immobilized 2-6-15 antigen. If desired, the antibody molecules directed against the 2-6-15 antigen can be isolated from the mammal (e.g., from the blood) and further purified by well known teclmiques, such as protein A chromatography to obtain the IgG fraction. At an appropriate time after immunization, e.g., when the anti-2-6-15 antigen antibody titers are highest, monoclonal antibodies can be prepared and screened.

Antibodies of the invention can be screened by the ability to bind the 2-6-15 antigen, the ability to compete with the mAb 2-6-15 epitope, or by the ability to deplete T cells about as efficiently or more efficiently than mAb 2-6-15 while resulting in about the same or less depletion of stem cells as mAb 2-6-15.

The preparation of an anti-2-6-15 mAb is described in section II below.

B. Hybridomas

Monoclonal antibodies of the invention can also be prepared and isolated using a technique which provides for the production of antibody molecules by continuous cell lines in culture. These include, but are not limited to, the hybridoma technique originally described by Kohler and Milstein (1975, *Nature* 256:495–497) (see also, Brown et al. (1981) *J. Immunol* 127:539–46; Brown et al. (1980) J Biol Chem 255:4980–83; Yeh et al. (1976) *PNAS* 76:2927–31; and Yeh et al. (1982) *Int. J. Cancer* 29:269–75), and the more recent human B cell hybridoma technique (Kozbor et al. (1983) *Immunol Today* 4:72), EBV-hybridoma technique (Cole et al. (1985), *Monoclonal Antibodies and Cancer Therapy*, Alan R. Liss, Inc., pp. 77–96), and trioma techniques.

The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al., (1977) *Somatic Cell Genet.*, 3:231–36). Briefly, an immortal cell line (typically myeloma cells) is fused to lymphocytes (typically splenocytes) from a mammal immunized with an immunogenic preparation of the present invention, as described above, and the culture supernatants of the resulting hybridoma cells are screened, as described above for screening of recombinant immunoglobulin libraries, to thereby identify an antibody of the invention.

Any of the many well known protocols used for fusing lymphocytes and immortalized cell lines can be applied for the purpose of generating an antibody of this invention (see, e.g., G. Galfre et al., (1977) *Nature* 266:55052; Gefter et al., *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a mycloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed).

Hybridoma cells producing a monoclonal antibody of the invention are detected by screening the hybridoma culture supernatants using the screening assays described above. For example, a primary screen can be performed to select antibodies that bind swine T cells. A secondary screen can then be performed to identify antibodies that bind immobilized epitope 2-6-15. The primary screen is preferably performed by FACS analysis.

Hybridoma cells that test positive in the above screening assays can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are well known (see, e.g., Lerner, *Yale J. Biol. Med.* and Kenneth, *Monoclonal Antibodies*, cited supra). Conditioned hybridoma culture supernatant containing the antibody can then be collected. Alternatively, the desired antibody can be produced by injecting the hybridoma cells into the peritoneal cavity of an unimmunized mouse. The hybridoma cells proliferate in the peritoneal cavity, secreting the antibody homolog, which accumulates as ascites fluid (see Lerner, *Yale J. Biol. Med.* and Kenneth, *Monoclonal Antibodies*, cited supra). The antibody is harvested by withdrawing the ascites fluid from the peritoneal cavity with a syringe. Accordingly, it will be understood by the ordinary skilled worker that monoclonal antibodies of the invention can be purified with ease from conditioned hybridoma culture supernatant or from ascites.

A monoclonal antibody prepared from a murine (or other non-human) hybridoma has the disadvantage that the antibody will be recognized as foreign in a subject of another species (e.g., a human). One approach to circumventing this problem is to engineer a recombinant chimeric or humanized antibody derived from the original non-human monoclonal antibody, as described in further detail below. As an alternative to humanizing a non-human monoclonal antibody, a human monoclonal directed against a human protein can be generated in transgenic mice carrying human antibody repertoires (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad Sci. USA* 81:6851–6855; Bruggeman et al. (1993) *Year Immunol* 7:33–40; Tuaillon et al. (1993) PNAS 90:3720–3724; Bruggeman et al. (1991) *Eur J Immunol* 21:1323–1326). A human antibody-transgenic mouse can be immunized with an immunogenic preparation of the present invention, as described above, and splenocytes from these immunized transgenic mice can then be used to create hybridomas, which are then screened to identify an antibody of the invention as described above.

C. Recombinant Combinatorial Antibody Libraries

Monoclonal antibodies can be prepared by constructing a recombinant combinatorial immunoglobulin library, such as a Fab phage display library, using immunoglobulin light chain and heavy chain cDNAs prepared from mRNA derived from lymphocytes of the immunized subject. Briefly, mRNA is isolated from a lymphocyte-containing cell population, such as bone marrow lymphocytes. First-strand cDNA is synthesized using primers specific for a constant region of the heavy chain (e.g., CH3) and the constant region of each of the κ and λ light chains. Using primers specific for the variable and constant regions, the heavy and light chain cDNAs are amplified by the polymerase chain reaction (PCR). The amplified DNA is then ligated into appropriate vectors for further manipulation in generating a library of display packages. Oligonucleotide primers useful in amplification protocols may be unique or degenerate and may incorporate inosine at degenerate positions. Restriction endonuclease recognition sequences may also be incorporated into the primers to allow for the cloning of the amplified fragment into a vector in a predetermined reading frame for expression.

The immunoglobulin library, e.g., a Fab library, is expressed by a population of display packages, preferably derived from filamentous phage, to form an antibody display library. Ideally, the display package comprises a system that allows for the sampling of a large, diverse antibody display library, rapid sorting after each affinity separation round, and easy isolation of the antibody genes from the purified display packages. In addition to commercially available kits for generating phage display libraries (e.g., the Pharmacia *Recombinant Phage Antibody System*, catalog no. 27-9400-01; and the Stratagene *SurfZAP*™ phage display kit, catalog no. 240612), examples of methods and reagents particularly amenable for use in generating antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibody Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFv gene subsequently cloned into the desired expression vector or phage genome. As generally described in McCafferty et al., *Nature* (1990) 348:552–554, complete VH and VL, domains of an antibody, joined by a flexible $(Gly_4\text{-}Ser)_3$ linker can be used to produce a single chain antibody expressed on the surface of a display package, such as a filamentous phage.

Once displayed on the surface of a display package (e.g., filamentous phage), the antibody library is screened to identify and isolate packages that express an antibody that binds the 2-6-15 antigen. In one embodiment, the primary screening of the library can involve panning with immobilized 2-6-15 antigen. Display packages expressing antibodies that bind immobilized 2-6-15 antigen can be selected. Soluble forms of the selected antibodies can then be generated and the soluble antibodies further selected in secondary screenings, e.g., by ELISA, radioimmunoassay and/or flow cytometry (FACS analysis).

Following screening and isolation of a monoclonal antibody of the invention from a recombinant immunoglobulin display library, nucleic acid encoding the selected antibody can be recovered from the display package (e.g., from the phage genome) and subcloned into other expression vectors by standard recombinant DNA techniques. The nucleic acid can be further manipulated (e.g., linked to nucleic acid encoding additional immunoglobulin domains, such as additional constant regions) and/or expressed in a host cell.

D. Chimeric and Humanized Antibodies.

The antibodies of the invention further encompass recombinant forms of antibodies, such as chimeric and humanized antibodies. When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the recipient.

Chimeric monoclonal antibodies can be produced by recombinant DNA techniques known in the art. For example, a gene encoding the constant region of a non-human antibody molecule is substituted with a gene encoding a human constant region. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041–1043); Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science* 229:1202–1207 and by Oi et al. (1986) *BioTechniques* 4:214. Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060).

E. Derivatized Antibodies

In another embodiment, this invention provides a derivatized antibody in which an antibody of the invention is functionally linked (by chemical coupling, genetic fusion or otherwise) to one or more other molecular entities, such as another antibody of the invention, a mimetic agent of the invention (described below), a detectable agent, a cytotoxic agent and/or a pharmaceutical agent.

One type of derivatized antibody is produced by crosslinking two or more antibodies (of the same type or of different types). Suitable crosslinkers include those that are heterobifunctional, having two distinctly reactive groups separated by an appropriate spacer (e.g.,m-maleimidobenzoyl-N-hydroxysuccinimide ester) or homobifunctional (e.g., disuccinimidyl suberate). Such linkers are available from Pierce Chemical Company, Rockford, Ill.

Useful detectable agents include fluorescent compounds. Exemplary fluorescent detectable agents include fluorescein, fluorescein isothiocyanate, rhodamine, 5-dimethylamine-1-napthalenesulfonyl chloride, phycoerythrin and the like.

An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody can also be derivatized with biotin, and detected through indirect measurement of avidin binding.

F. Antibody Mimetic Agents

The invention further encompasses non-antibody molecules that mimic the epitope binding specificity of the antibodies described herein. These agents are referred to herein as "antibody mimetic agents". The antibody mimetic agents of the invention are non-antibody compounds that bind the 2-6-15 antigen. A preferred antibody mimetic agent of the invention binds an epitope recognized by the monoclonal 2-6-15, referred to herein as a "2-6-15 mimetic agent". Preferred antibody mimetic agents, e.g., 2-6-15 mimetic agents, deplete swine white blood cell populations when administered in vivo. The most preferred antibody mimetic agents of the invention display the properties of one or more antibodies of this invention (e.g., the monoclonal 2-6-15).

An antibody mimetic agent of this invention can be produced by synthesizing a plurality of peptides (e.g., 5–20 amino acids in length), semi-peptidic compounds or non-peptidic, organic compounds, and then screening those compounds for their ability to bind the immobilized 2-6-15 antigen, using assays described herein. For general descriptions of peptide library construction and screening see U.S. Pat. No. 4,833,092; Scott, J. K. and Smith, G. P. (1990) *Science* 249:86–90; Devlin, J. J. et al. (1990) *Science* 249:404–407. Alternatively, the agents can be screened for their ability to competitively inhibit binding of an antibody of the present invention to swine T cells. For example, a 2-6-15 mimetic agent can be identified based upon its ability to inhibit the binding of the monoclonal antibody 2-6-15 to either the 2-6-15 antigen or swine T cells. Preferably, FACS analysis is used to determine whether an antibody mimetic agent can competitively inhibit the binding of an antibody of the present invention to swine T cells.

G. Recombinant Expression of Antibodies

In one embodiment, an antibody of the invention is produced in quantity by recombinant expression of immunoglobulin light and heavy chain genes in a host cell. To express an antibody recombinantly, a host cell is transfected with DNA encoding the immunoglobulin light and heavy chains of the antibody in a form suitable for expression of the light and heavy chains in the host cell. Recombinant antibodies can be produced by well known genetic engineering techniques (see, e.g., U.S. Pat. No. 4,816,397).

When an antibody (or antibody fragment) of the invention is isolated from a recombinant immunoglobulin display library, as described above, DNA encoding the light and heavy chains of a selected antibody of interest can be recovered from the display package (e.g., from the genome of the filamentous phage) and, if desired, further manipulated. Such manipulation may involve conversion of a partial antibody chain to a full-length antibody chain. For example, when a Fab expression library is screened, the isolated DNA encoding the heavy chain of the Fab can be converted to a full-length heavy chain gene by operatively linking the DNA to another DNA molecule encoding the additional heavy chain constant regions. Similarly, if a scFv library is screened, the portions of the isolated DNA encoding the linked VL and VH regions of the scFv can be separated and the separate VL- and VH- encoding DNA molecules can then be operatively linked to other DNA molecules encoding the appropriate light and heavy chain constant regions to produce full-length antibody genes.

Alternatively, when an antibody of the invention is isolated by screening hybridomas, as described above, cDNA or genomic DNA encoding the immunoglobulin light and heavy chains of a selected antibody, or a portion thereof, can be isolated from the hybridoma cell by standard molecular biology techniques.

Following isolation, and, if desired, further manipulation, cDNAs or genomic DNAs encoding partial or full-length light or heavy chains are inserted into expression vectors so that both genes are operatively linked to their own transcriptional and translational control sequences. The expression vector and expression control sequences are chosen to be compatible with the expression host cell used. Typically, both genes are inserted into the same expression vector. For expression of the light and heavy chains, the expression vector(s) is transfected into a host cell by standard techniques. Prokaryotic or eukaryotic host cells may be used. The terms "transfection" or "transfected into" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Expression of antibodies in eukaryotic host cells is preferred because such cells are more likely than prokaryotic cells to assemble and secrete a properly folded and immunologically active antibody. However, any antibody produced that is inactive due to improper folding may be renaturable according to well known methods (see e.g., P. S. Kim and R. L. Baldwin (1982) *Ann. Rev. Biochem.* 51:45989).

Host cells can also be used to produce portions of intact antibodies, such as light chain dimers or heavy chain dimers, which are encompassed by the term "antibody" as used herein. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to the 2-6-15 antigen.

The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the 2-6-15 antigen.

II. Preparation and Characterization of MAB 2-6-15

The antibody 89BH 2-6-15 (mAb 2-6-15) was raised in C3H mice immunized with $SLA^{dd}$ swine lymphocytes in this laboratory. Analyses by Flow Cytometry (FACS) have shown that this mAb reacts with all porcine T-cells in the peripheral blood and in several lymphoid tissues (lymph node, spleen, intraepithelial lymphocytes [IEL] of the gut and Peyer's patches) but that it does not stain all thymocytes. Two-color FACS analysis with an anti-CD2 mAb (MSA4) revealed that 2-6-15 is not directed against the CD2 antigen. The staining pattern on immature thymocytes and the 98% staining of the IELs suggest that 2-6-15 may be directed against a CD3 determinant, although staining of platelets argues against this possibility.

The 2-6-15 mAb stimulates peripheral blood lymphocytes in vitro with maximum response after 48 hours; it inhibits allogenic MLR responses. In vivo administration of 2-6-15 leads to a rapid (24) hours drop in white blood cells of up to 80% and to a decrease in platelets, both of which are dose dependent. FACS studies on PBL after in vivo administration have shown that this antibody induces modulation of CD2, CD4 and CD8 antigens. Marked depletion of all cells from lymph node and thymus was also observed. Infusion of 2-6-15 in a dose of 10 mg/kg on day-2 led to marked prolongation of fully mismatched skin graft survival (20 days vs. 7 days in controls). Therefore this mAb appears to have a unique specificity and immunosuppressive activity.

III. Deposit of MAB 2-6-15 mAb-2-6-15 was deposited with the ATCC on Jun. 1, 1995, and was assigned ATCC deposit Number HB11914

VI. The induction of tolerance with bone marrow transplantation (coupled with the administration of mAb 2-6-15 to control GVHD)

The following procedure was designed to lengthen the time an implanted organ (a xenograft) survives in a xenogeneic host prior to rejection and to inhibit GVHD. The organ can be any organ, e.g., a liver, e.g., a kidney, e.g., a heart. The main strategies are elimination of natural antibodies by organ perfusion, transplantation of tolerance-inducing bone marrow, the implantation of donor stromal tissue, the administration of a short course of a help reducing agent at about the time of introduction of the graft, and the administration of anti-2-6-15 antibodies to control GVHD as described above. Preparation of the recipient for transplantation includes any or all of these steps. Preferably they are carried out in the following sequence.

First, a preparation of horse anti-human thymocyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. Of equal importance, the ATG preparation also eliminates natural killer (NK) cells. NK cells probably have no effect on the implanted organ, but would act immediately to reject the newly introduced bone marrow. Anti-human ATG obtained from any mammalian host can also be used, e.g., ATG produced in pigs, although thus far preparations of pig ATG have been of lower titer than horse-derived ATG. ATG is superior to anti-NK monoclonal Antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks. Alternatively, e.g. if this approach is not successful, and tolerance (as measured by donor skin graft acceptance, specific cellular hyporesponsiveness in vitro, and humoral tolerance) is not induced in these animals, the approach can be modified to include host thymectomy. In thymectomized recipients, host T cells do not have an opportunity to differentiate in a host thymus, but must differentiate in the donor thymus. If this is not possible, then the animal has to rely on donor T cells developing in the donor thymus for immunocompetence. Immunocompetence can be measured by the ability to reject a non-donor type allogeneic donor skin graft, and to survive in a pathogen-containing environment.

It may also be necessary or desirable to splenectomize the recipient in order to avoid anemia.

Second, the recipient is administered low dose radiation to create hematopoietic space. A sublethal dose of between 100 rads and 400 rads whole body radiation has been found effective for this purpose. Thymic irradiation, e.g., 700 rads of local thymic radiation, can be administered as well.

Third, natural antibodies are absorbed from the recipient's blood by hemoperfusion of a liver of the donor species. Pre-formed natural antibodies (nAB) are the primary agents of graft rejection. Natural antibodies bind to xenogeneic endothelial cells and are primarily of the IgM class. These antibodies are independent of any known previous exposure to antigens of the xenogeneic donor. B cells that produce these natural antibodies tend to be T cell-independent, and are normally tolerized to self antigen by exposure to these antigens during development. The mechanism by which newly developing B cells are tolerized is unknown. The liver is a more effective absorber of natural antibodies than the kidney.

The fourth step in the non-myeloablative procedure is to implant donor stromal tissue, preferably obtained from fetal liver, thymus, and/or fetal spleen, into the recipient, preferably in the kidney capsule. Stem cell engraftment and hematopoiesis across disparate species barriers is enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension.

Fifth, bone marrow cells (BMC), or another source of hematopoietic stem cells, e.g., a fetal liver suspension, of the donor are injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

Sixth, a short course of a help reducing agent, e.g., a short course of high dose CsA is administered to the recipient. As is described above, the course is begun at about the time of implantation, or a little before, and is continued for a time about equal to the time it takes for a mature T cell to be stimulated and initiate rejection. While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

"Help reduction", as used herein, means the reduction of T cell help by the inhibition of the release of at least one cytokine, e.g. , any of IL-2, IL-4, IL-6, gamma interferon, or TNF, from T cells of the recipient at the time of the first exposure to an antigen to which tolerance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing tolerance.

"A help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in tolerance. The help reducing agent should be administered in the absence of treatments which promote cytokine, e.g., IL-2, release. Putative agents help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a class II matched class I and minor antigen mismatched donor monkey into the recipient. Tolerance to the donor kidney (as indicated by prolonged acceptance of the graft) is indicative that the putative agent is, at the dosage tested, a help reducing agent.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient. Experiments with cyclosporine A (10 mg/kg) in pigs show that 6 days is not sufficient. Other experiments in monkeys show that IL-2 administered on day 8, 9, or 10 of cyclosporine A treatment will result in rejection of the transplanted tissue. Thus, 8, 9, or 10 days is probably not sufficient in pigs. In monkeys, a dose of 10 mg/kg cyclosporine with a blood level of about 500–1,000 ng/ml is sufficient to induce tolerance to class II matched class I and minor antigen mismatched kidneys. The same blood level, 500–1,000 ng/ml, is sufficient to induce tolerance in pigs. Long-term administration of mg/kg prevents rejection (by long term immune suppression) but does not result in tolerance.

Finally, an antibody which binds a donor T cell antigen can be administered to a recipient of a donor graft. For example, in one embodiment, the donor tissue, e.g., hematopoietic stem cells, can be pretreated with an antibody, e.g., a monoclonal antibody, which binds a donor, e.g., a swine, e.g., a miniature swine, T cell antigen, e.g., the 2-6-15 antigen. The pretreated donor tissue can then be introduced in a recipient to inhibit GVHD of an implanted graft. In addition, the antibody which binds a donor T cell antigen can be administered to the recipient in conjunction with the pretreated donor tissue to inhibit GVHD. In another embodiment, the antibody which binds a donor T cell antigen can be directly administered to the graft recipient without antibody-pretreating the donor tissue.

While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

The method of introducing bone marrow cells may be altered, particularly by (1) increasing the time interval between injecting hematopoietic stem cells and implanting the graft; (2) increasing or decreasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the graft donor are preferable, hematopoietic stem cells may be obtained from other individuals or species, or from aenetically-engineered inbred donor strains, or from in vitro cell culture.

Methods of preparing the recipient for transplant of hematopoietic stem cells may be varied. For instance, recipient may undergo a splenectomy or a thymectomy. The latter would preferably be administered prior to the non-myeloablative regimen, e.g., at day -14.

Hemoperfusion of natural antibodies may: (1) make use of other vascular organs, e.g., liver, kidney, intestines; (2) make use of multiple sequential organs; (3) vary the length of time each organ is perfused; (4) vary the donor of the perfused organ. Irradiation of the recipient may make use of: (1) varying the absorbed dose of whole body radiation below the sublethal range; (2) targeting different body parts (e.g., thymus, spleen); (3) varying the rate of irradiation (e.g., 10 rads/min, 15 rads/min); or (4) varying the time interval between irradiation and transplant of hematopoietic stem cells; any time interval between 1 and 14 days can be used, and certain advantages may flow from use of a time interval of 4–7 days. Antibodies introduced prior to hematopoictic cell transplant may be varied by: (1) using monoclonal antibodies to T cell subsets or NK cells (e.g., anti-NKH1$_A$, as described by U.S. Pat. No. 4,772,552 to Hercend, et al., hereby incorporated by reference); (2) preparing anti-human ATG in other mammalian hosts (e.g., monkey, pig, rabbit, dog); or (3) using anti-monkey ATG prepared in any of the above mentioned hosts.

The methods of the invention may be employed with other mammalian recipients (e.g., rhesus monkeys) and may use other mammalian donors (e.g., primates, sheep, or dogs). As an alternative or adjunct to hemoperfusion, host antibodies can be depleted by administration of an excess of hematopoietic cells.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus or fetal spleen as a source of stromal tissue.

EXAMPLE

Two miniature swine recipients received grafts from a third animal. The recipients and donor were MHC matched but differed at minor loci. The control animal (which did not receive mAb 2-6-15 treatment developed GVHD. The second recipient, which was treated with mAb 2-6-15 failed to develop GVHD.

OTHER EMBODIMENTS

The invention also includes antibodies of the invention, hybridomas which produce the antibodies, and DNA which encodes the antibodies.

The methods of the invention are particularly useful for replacing a tissue or organ afflicted with a neoplastic disorder, particularly a disorder which is resistant to normal modes of therapy, e.g., chemotherapy or radiation therapy. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Tolerance, as used herein, refers not only to complete immunologic tolerance to an antigen, but to partial immunologic tolerance, i.e., a degree of tolerance to an antigen which is greater than what would be seen if a method of the invention were not employed.

As is discussed herein, it is often desirable to expose a graft recipient to irradiation in order to promote the development of mixed chimerism. It is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft or allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. For example, a single dose of 700 rads can be replaced with, e.g., two fractions of 350 rads, or seven fractions of 100 rads. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

Much or all of the preparative regimen can be delivered or administered to a recipient, e.g., an allograft or xenograft recipient, within a few days, preferably within 72, 48, or 24 hours, of transplantation of tolerizing stem cells and/or the graft. This is particularly useful in the case of humans receiving grafts from cadavers. Accordingly, in any of the methods of the invention calling for the administration of treatments prior to the transplant of stem cells and/or a graft, e.g., treatments to inactivate or deplete host antibodies, treatments to inactivate host T cells or NK cells, or irradiation, the treatment(s) can be administered, within a few days, preferably within 72, 48, or 24 hours, of transplantation of the stem cells and/or the graft. In particular, primate, e.g., human, recipients of allografts can be given any or all of treatments to inactivate or deplete host antibodies, treatments to inactivate host T cells or NK cells, or irradiation, within a few days, preferably within 72, 48, or 24 hours, of transplantation of stem cells and/or the graft. For example, treatment to deplete recipient T cells and/or NK cells, e.g., administration of ATG, can be given on day -2, -1, and 0, and WBI, thymic irradiation, and stem cell, e.g., bone marrow stem cells, administered on day 0. (The graft, e.g., a renal allograft, is transplanted on day 0).

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

As is discussed in PCT/US94/01616, hereby incorporated by reference, the engraftment of exogenously supplied hematopoietic stem cells can be promoted by treating the recipient of the cells so as to induce hematopoietic space in the recipient. Hematopoietic space is commonly induced by radiation, but other procedures can replace or reduce the need for WBI. For example, space can be created by treating the recipient with a monoclonal antibody against MIC class I antigens expressed by the recipient (see e.g., Voralia, M. et al. (1987) Transplantation 44:487) or space can be created by treating the recipient with myelosuppressive drugs (see e.g., Lapidot, T. et al. (1990) *Proc. Natl. Acad. Sci. USA* 87:4595). As for WBI, space created within the recipient for bone marrow transplantation by other mechanisms (e.g., anti-MHC class I treatment or myclosuppressive drugs) can be assessed by monitoring WBC counts in the recipient.

Some of the methods described herein use lethal irradiation to create hematopoietic space, and thereby prepare a recipient for the administration of xenogeneic, stem cells. In any of the methods described herein, particularly primate or clinical methods, it is preferable to create hematopoietic space for the administration of such cells by non-lethal means, e.g., by administering sub-lethal doses of irradiation, bone marrow depleting drugs, or antibodies. The use of sublethal levels of bone marrow depletion allows the generation of mixed chimerism in the recipient. Mixed chimerism is generally preferable to total or lethal ablation of the recipient bone marrow followed by complete reconstitution of the recipient with administered stem cells.

Alternative methods for the inactivation of thymic T cells are also included in embodiments of the invention. Some of the methods described herein include the administration of thymic irradiation to inactivate host thymic-T cells or to otherwise diminish the host's thymic-T cell mediated responses to donor antigens. It has been discovered that the thymic irradiation called for in allogeneic or xenogeneic methods of the invention can be supplemented with, or replaced by, other treatments which diminish (e.g., by depleting thymic-T cells and/or down modulating one or more of the T cell receptor (TCR), CD4 co-receptor, or CD8 co-receptor) the host's thymic-T cell mediated response. For example, thymic irradiation can be supplemented with, or replaced by, anti-T cell antibodies (e.g., anti-CD4 and/or anti-CD8 monoclonal antibodies) administered a sufficient number of times, in sufficient dosage, for a sufficient period of time, to diminish the host's thymic-T cell mediated response.

For best results, anti-T cell antibodies should be administered repeatedly. E.g., anti-T cell antibodies can be administered one, two, three, or more times prior to donor bone marrow transplantation. Typically, a pre-bone marrow transplantation dose of antibodies will be given to the patient about 5 days prior to bone marrow transplantation. Additional, earlier doses 6, 7, or 8 days prior to bone marrow transplantation can also be given. It may be desirable to administer a first treatment then to repeat pre-bone marrow administrations every 1–5 days until the patient shows excess antibodies in the serum and about 99% depletion of peripheral T cells and then to perform the bone marrow transplantation. Anti-T cell antibodies can also be administered one, two, three, or more times after donor bone marrow transplantation. Typically, a post-bone marrow transplant treatment will be given about 2–14 days after bone marrow transplantation. The post bone marrow administration can be repeated as many times as needed. If more than one administration is given the administrations can be spaced about 1 week apart. Additional doses can be given if the patient appears to undergo early or unwanted T cell recovery. Preferably, anti-T cell antibodies are administered at least once (and preferably two, three, or more times) prior to donor bone marrow transplantation and at least once (and preferably two, three, or more times) after donor bone marrow transplantation.

A depression in WBC corresponds to a window for stem cell engraftment

As described in PCT/US94/01616, hereby incorporated by reference, it has been discovered that there is a permissible time period ("window") for hematopoietic stem cell engraftment following the creation of space (e.g., by whole body irradiation) for the donor hematopoietic stem cells in a recipient. It has further been discovered that space created for hematopoietic stem cell engraftment can be monitored over time by monitoring peripheral white blood cell levels in a recipient. The myelosuppressive treatment sufficient to create hematopoietic space generally results in a reduction in white blood cell (WBC) levels (as revealed, e.g., by WBC counts) and the WBC reduction serves as a marker for the presence of hematopoietic space. The marker is a conservative one since WBC counts may recover at a time when space is still present in an animal.

Accordingly, in any method which involves hematopoietic stem cell transplantation, and thus also requires the creation of hematopoietic space in a recipient, transplantation can be performed during the permissible window for engraftment following creation of space for the hematopoietic stem cells. Likewise, in any method in which space is created for exogenously administered hematopoietic stem cells, white blood cell levels can be followed to monitor space for the donor hematopoietic stem cells (i.e., to assess the permissible window for engraftment). Examples of procedures involving hematopoietic stem cell transplantation include: 1) conditioning of a recipient for an allo- or xenograft in which hematopoietic stem cell transplantation is performed in conjunction with transplantation of another allo- or xenograft; 2) treatment of various hematopoietic disorders, including leukemias, lymphomas and other hematopoietic malignancies and genetic hematopoietic disorders (e.g., adenosine deaminase deficiency, bare lymphocyte syndrome and other congenital immunodeficiency diseases) in which hematopoietic stem cell transplantation is performed therapeutically; and 3) transplantation of genetically modified hematopoietic stem cells (e.g., genetically modified autologous hematopoietic stem cells) to deliver a gene product to a recipient (e.g., as gene therapy).

Other embodiments are within the following claims.

What is claimed is:

1. A method of preparing swine donor tissue which comprises hematopoietic stem cells and T cells for tranplantation into a recipient mammal other than a swine, comprising:
    contacting said swine donor tissue which comprises hematopoietic stem cells and T cells with an antibody which binds the epitope recognized by the mAb 2-6-15 monoclonal antibody and wherein said binding faciltates depletion of said T cells about as efficiently or more efficently than does the mAb 2-6-15 monoclonal antibody while resulting in about the same or less depletion of stem cells as does the the mAb 2-6-15 monoclonal antibody, thereby preparing swine donor tissue for transplantation into a recipient mammal other than a swine.

2. A preparation comprising hematopoietic stem cells, swine T cells, and an antibody which binds the epitope recognized by the mAb 2-6-15 monoclonal antibody and wherein said binding facilitates depletion of said T cells about as efficiently or more efficiently than does the mAb 2-6-15 monoclonal antibody while resulting in about the same or less depletion of stem as does the mAb 2-6-15 monoclonal antibody.

3. A preparation of T cell-depleted swine hematopoietic stem cells, wherein the preparation is made by a method comprising contacting a population of swine hematopoietic stem cells and swine T cells with an antibody which binds the epitope recognized by the mAb 2-6-15 monoclonal antibody and wherein said binding facilitates depletion of said T cells about as efficiently or more efficiently than does the mAb 2-6-15 monoclonal antibody while resulting in about the same or less depletion of stem cells as does the mAb 2-6-15 monoclonal antibody, thereby depleting the T cells.

4. The preparation of claim 3, wherein at least 80% of said T cells are depleted.

5. A method of reducing graft-versus-host disease in a mammal which is the recipient of a swine graft, comprising:
    introducing "a preparation comprising swine bone marrow cells and swine T cells to" said recipient mammal;
    implanting said swine graft into said recipient mammal; and
    administering to said recipient mammal an antibody which binds the epitope recognized by the mAb 2-6-15 monoclonal antibody and wherein said binding facilitates depletion of said T cells about as efficiently or more efficiently than does the mAb 2-6-15 monoclonal antibody while resulting in about the same or less depletion of stem cells as does the mAb 2-6-15 monoclonal antibody,
whereby said graft-versus-host disease is reduced in comparison to engraftment in the absence of treatment with said antibody.

6. A method of reducing graft-versus-host disease in a mammal which is the recipient of a swine graft, comprising:
    contacting a preparation which comprises swine bone marrow cells and swine T cells with an antibody which binds the epitope recognized by the mAb 2-6-15 monoclonal antibody and wherein said binding facilitates depletion of said T cells about as efficiently or more efficiently than does the mAb 2-6-15 monoclonal antibody while resulting in about the same or less depletion of stem cells as does the mAb 2-6-15 monoclonal antibody;
    introducing said antibody-treated preparation into said mammal; and implanting said swine graft into said recipient mammal, whereby said graft-versus-host disease is reduced in comparison to engraftment with swine bone marrow cells which have not been treatment said antibody.

7. A method of reducing graft-versus-host disease in a mammal which is the recipient of a swine graft, comprising:

contacting a preparation which comprises swine bone marrow cells and swine T cells with an antibody which binds the epitope recognized by the mAb 2-6-15 monoclonal antibody and wherein said binding facilitates depletion of said T cells about as efficiently or more efficiently than does the mAb 2-6-15 monoclonal antibody while resulting in about the same or less depletion of stem as does the mAb 2-6-15 monoclonal antibody;

introducing said antibody-treated preparation into said recipient mammal;

implanting said swine graft into said recipient mammal; and administering to said recipient mammal an antibody which binds the epitope recognized by the mAb 2-6-15 monoclonal antibody and wherein said binding facilitates depletion of said T cells about efficiently or more efficently than the mAb 2-6-15 monoclonal antibody while resulting in about the same or less depletion of stem cells as the mAb 2-6-15 monoclonal antibody, whereby said graft-versus-host disease is reduced in comparison to engraftment in the absence of treatment with said antibody.

8. The method of claim 1, wherein said antibody is mAb 2-6-15.

9. The method of claim 2, wherein said antibody is mAb 2-6-15.

10. The method of claim 3, wherein said antibody is mAb 2-6-15.

11. The method of claim 5, wherein said antibody is mAb 2-6-15.

12. The method of claim 6, wherein said antibody is mAb 2-6-15.

13. The method of claim 7, wherein said antibody is mAb 2-6-15.

14. The method of claim 5, wherein said mammal is a human.

15. The method of claim 5, wherein said swine graft is isolated from a miniature swine graft.

16. The method of claim 1, wherein said mammal is a human.

17. The method of claim 1, wherein said swine preparation is isolated from a mimiature swine.

18. The method of claim 7, wherein said mammal is a human.

19. The method of claim 1, wherein said swine preparation is isolated from a mimiature swine.

* * * * *

UNITED STATES PATENT AND TRADEMARK OFFICE
CERTIFICATE OF CORRECTION

| | | |
|---|---|---|
| PATENT NO. | : 5,843,425 | Page 1 of 1 |
| APPLICATION NO. | : 08/461693 | |
| DATED | : December 1, 1998 | |
| INVENTOR(S) | : David H. Sachs, J. Scott Arn and Thomas Lorf | |

It is certified that error appears in the above-identified patent and that said Letters Patent is hereby corrected as shown below:

In column 1, after line 22, please insert the following paragraph:

--This invention was made with Government support under Grant No. CA061537 awarded by the National Institutes of Health. The Government has certain rights in this invention.--

Signed and Sealed this

Twentieth Day of July, 2010

David J. Kappos
*Director of the United States Patent and Trademark Office*